(12) United States Patent
Wittnebel et al.

(10) Patent No.: US 12,070,425 B2
(45) Date of Patent: Aug. 27, 2024

(54) PATIENT INTERFACE FOR OPHTHALMIC LASER SURGICAL SYSTEM

(71) Applicant: Alcon Inc., Fribourg (CH)

(72) Inventors: Michael Wittnebel, Hirschaid (DE); Mario Abraham, Burgthann (DE)

(73) Assignee: ALCON INC., Fribourg (CH)

( * ) Notice: Subject to any disclaimer, the term of this patent is extended or adjusted under 35 U.S.C. 154(b) by 244 days.

(21) Appl. No.: 17/406,135

(22) Filed: Aug. 19, 2021

(65) Prior Publication Data

US 2022/0062038 A1 Mar. 3, 2022

Related U.S. Application Data

(60) Provisional application No. 63/070,783, filed on Aug. 26, 2020.

(51) Int. Cl.
*A61F 9/009* (2006.01)
*A61B 18/22* (2006.01)
*A61F 9/008* (2006.01)

(52) U.S. Cl.
CPC .............. *A61F 9/009* (2013.01); *A61B 18/22* (2013.01); *A61F 9/00825* (2013.01)

(58) Field of Classification Search
CPC ..................................................... A61F 9/009
See application file for complete search history.

(56) References Cited

U.S. PATENT DOCUMENTS

| 2004/0196431 | A1 | 10/2004 | Farberov |
| 2007/0255119 | A1* | 11/2007 | Mordaunt ........... A61F 9/00821 600/300 |
| 2010/0228236 | A1* | 9/2010 | Muhlhoff ................ A61F 9/009 606/4 |
| 2011/0009851 | A1* | 1/2011 | Donitzky ............ A61F 9/00825 606/4 |
| 2011/0112519 | A1 | 5/2011 | Donitzky et al. |
| 2016/0331586 | A1 | 11/2016 | Deisinger |
| 2017/0281407 | A1* | 10/2017 | Garcia ..................... A61B 3/14 |
| 2019/0175400 | A1 | 6/2019 | Loerner et al. |

FOREIGN PATENT DOCUMENTS

WO 2013053367 A1 4/2013

* cited by examiner

*Primary Examiner* — Lynsey C Eiseman
*Assistant Examiner* — Skylar Lindsey Christianson (57) ABSTRACT

In certain embodiments, a patient interface for an ophthalmic laser system comprises an interface portion and an attachment portion. The interface portion comprises a contact portion, a cone wall, and one or more structures. The contact portion has an abutment face that is configured to be in contact with the cornea of an eye. The cone wall is disposed outwardly from the contact portion and defines a cone interior. The cone wall has an inner surface and an outer surface, where the inner surface defines the cone interior. The cone wall has an upper portion and a lower portion, where the lower portion is coupled to the contact portion. The one or more structures direct light from the cone wall towards the cone interior. The attachment portion affixes the interface portion to the cornea of the eye.

23 Claims, 7 Drawing Sheets

PATIENT INTERFACE FOR OPHTHALMIC LASER SURGICAL SYSTEM

TECHNICAL FIELD

The present disclosure relates generally to ophthalmic laser surgical systems, and more particularly to patient interfaces for ophthalmic laser surgical systems.

BACKGROUND

Certain ophthalmic laser surgical systems generate a pulsed laser beam to perform a surgical procedure on an eye. In some procedures, the laser beam creates photodisruptions at specific points in the eye according to a treatment pattern. The eye should be stabilized throughout the procedure so the laser beam can create photodisruptions that precisely match the pattern.

A patient interface (PI) is usually used to hold the eye in position during the procedure. The patient interface is typically affixed to the eye by a vacuum to secure the eye in place to allow the laser beam to operate on the surgical site during the procedure. In some systems, a light source illuminates the surgical site through a patient interface. The illumination may improve imaging of the surgical site by a camera. The illumination may also allow for identification of features used to align the eye with the treatment pattern.

BRIEF SUMMARY

In certain embodiments, a patient interface for an ophthalmic laser system comprises an interface portion and an attachment portion. The interface portion comprises a contact portion, a cone wall, and one or more structures. The contact portion has an abutment face that is configured to be in contact with the cornea of an eye. The cone wall is disposed outwardly from the contact portion and defines a cone interior. The cone wall has an inner surface and an outer surface, where the inner surface defines the cone interior. The cone wall has an upper portion and a lower portion, where the lower portion is coupled to the contact portion. The one or more structures direct light from the cone wall towards the cone interior. The attachment portion affixes the interface portion to the cornea of the eye.

Embodiments may include none, one, some, or all of the following features:

The cone wall has a frustoconical or cylindrical shape.
The one or more structures comprise a stepped feature of the inner surface of the cone wall.
The one or more structures comprise a stepped feature formed by at least two materials of the cone wall, where the materials have different indices of refraction.
The one or more structures comprise a diffusion structure disposed at the inner surface of the cone wall. The diffusion structure diffuses light traveling from the cone wall towards the cone interior.
The one or more structures comprise a reflective structure disposed at the cone wall. The reflective structure reflects light towards the cone interior. The reflective structure may be disposed at the inner surface and/or the outer surface of the cone wall.
The one or more structures direct light within the cone wall towards the lower portion. The one or more structures may comprise a light guide that directs light within the cone wall towards the lower portion.
The one or more structures direct light within the cone wall towards the lower portion. The one or more structures may comprise reflective structures that direct light within the cone wall towards the lower portion. The reflective structures may comprise an inner reflective structure and an outer reflective structure. The inner reflective structure is disposed at the inner surface of the cone wall, and reflects light towards the outer reflective structure. The outer reflective structure is disposed at the outer surface of the cone wall, and reflects light towards the inner reflective structure, and through a portion of the inner surface that is free from the inner reflective structure. The one or more structures may further comprise a diffusion structure disposed at the portion of the inner surface that is free from the inner reflective structure, where the diffusion structure diffuses light travelling from the cone wall towards the cone interior.
The one or more structures comprise a structure disposed at the contact portion of the interface portion. The structure directs light towards a surgical site portion of the contact portion. The one or more structures may further comprise a reflective structure disposed at the portion of the abutment face adjacent to the cone wall.
The one or more structures comprise a refractive structure that refracts light towards a surgical site portion of the contact portion.
The one or more structures comprise a scattering structure that scatter lights towards a surgical site portion of the contact portion.

In certain embodiments, a patient interface for an ophthalmic laser system comprises an interface portion and an attachment portion. The interface portion comprises a contact portion, a cone wall, and one or more structures. The contact portion has an abutment face that is configured to be in contact with the cornea of an eye. The cone wall is disposed outwardly from the contact portion and defines a cone interior. The cone wall has an inner surface and an outer surface, where the inner surface defines the cone interior. The cone wall has an upper portion and a lower portion, where the lower portion is coupled to the contact portion. The one or more structures comprises a light guide that directs light within the cone wall from the upper portion towards the lower portion. The attachment portion affixes the interface portion to the cornea of the eye.

Embodiments may include none, one, some, or all of the following features:

The one or more structures further comprise a scattering structure that scatters light towards a surgical site portion of the contact portion.
The one or more structures further comprise a scattering structure that scatters light towards the eye.
The one or more structures further comprise a reflective structure that reflects light towards a surgical site portion of the contact portion.
The light guide is curved to direct light towards a surgical site portion of the contact portion.

DESCRIPTION OF EXAMPLE EMBODIMENTS

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

In certain ophthalmic laser surgical systems, a light source illuminates a surgical site through a patient interface. An issue that may arise is that the patient interface modifies the light such that the resulting illumination at the surgical site is not sufficiently bright and/or homogeneous. Certain embodiments of the patient interfaces described herein address this issue.

Figure 1:
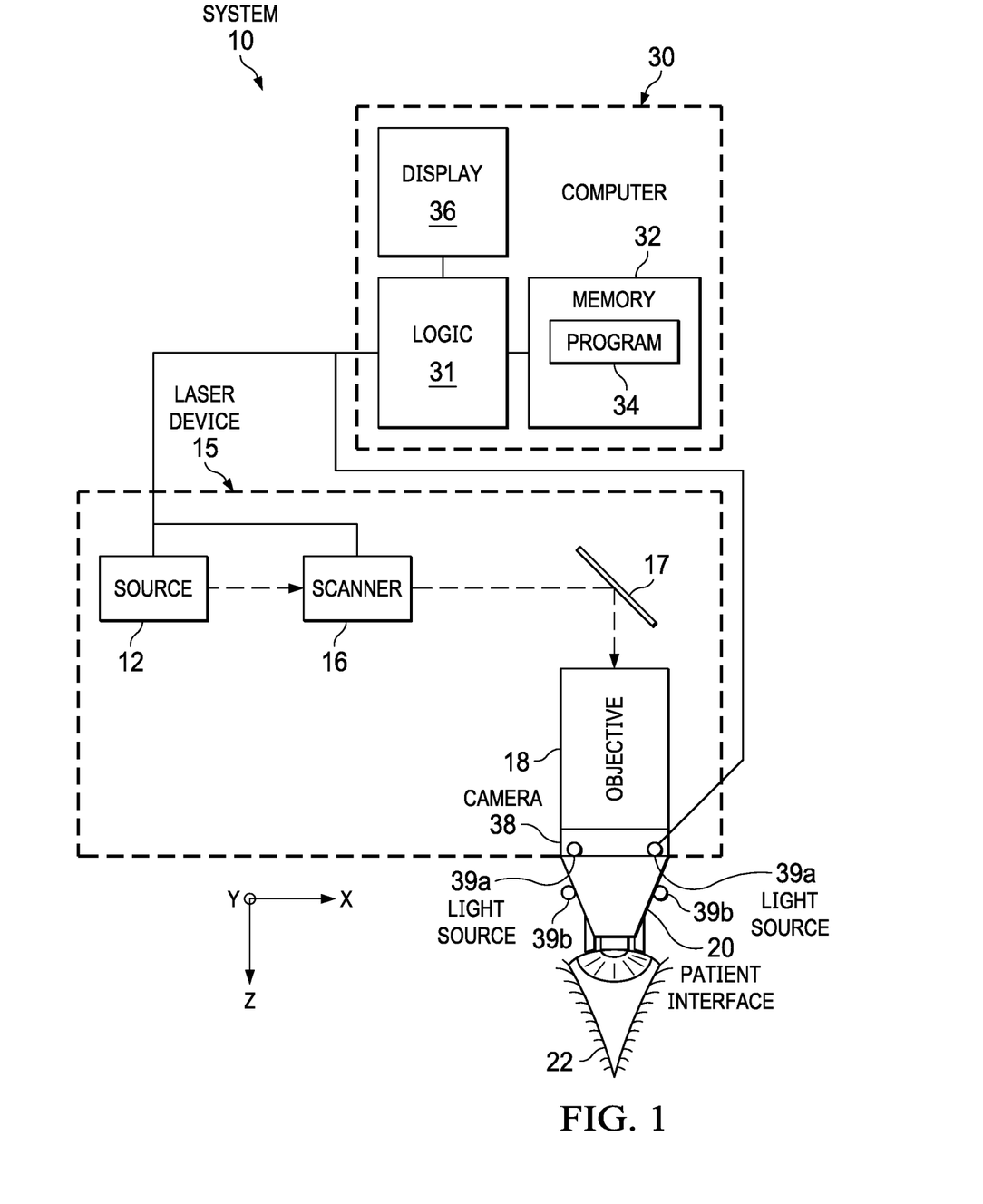
FIG. 1 illustrates an example of an ophthalmic surgical system with a patient interface that facilitates illumination of a surgical site according to certain embodiments.

FIG. 1 illustrates an example of an ophthalmic surgical system 10 with a patient interface 20 that facilitates illumination of a surgical site according to certain embodiments. In the embodiments, patient interface 20 includes an interface portion with a cone wall and a contact portion. The cone wall has a shape that defines a cone interior. Patient interface 20 also includes one or more structures that direct light from the cone wall towards the cone interior and/or central area of the contact portion to illuminate the surgical site portion of interface 20 (e.g., a portion interface 20 in contact with the surgical site of the eye), which may yield brighter, more homogeneous illumination at the surgical site. The improved illumination may allow a camera to better image the surgical site and may allow for more reliable and/or effective identification of features to properly align the eye with the laser treatment.

In the illustrated example, system 10 includes a laser device 15, a patient interface 20, a camera 38, and a control computer 30, coupled as shown. Computer 30 includes logic 31, a memory 32 (which stores a computer program 34), and a display 36, coupled as shown. Laser device 15 includes controllable components, such as a laser source 12, a scanner 16, one or more optical elements 17, a focusing objective 18, and a light source 39, coupled as shown. Patient interface 20 is coupled as shown.

Turning to the parts of system 10, laser source 12 generates a laser beam with ultrashort pulses. An ultrashort pulse refers to a light pulse that has a duration less than a nanosecond, such as on the order of picoseconds, femtoseconds, or attoseconds. The laser beam may have any suitable wavelength, such as a wavelength in the range of 300 to 1500 nanometers (nm), e.g., a wavelength in the range of 300 to 650, 650 to 1050, 1050 to 1250, and/or 1250 to 1500 nm, such as 340 to 350 nm, e.g., 347 nm±1 nm. The focal point of the laser beam may create a laser-induced optical breakdown (LIOB) in tissue (e.g., the cornea) to yield a photodisruption in the tissue. The laser beam may be precisely focused to yield precise photodisruptions, which may reduce or avoid unnecessary destruction of other tissue.

Scanner 16 transversely and longitudinally directs the focal point of the laser beam. The longitudinal direction refers to the direction of the laser beam propagation, also known as the z-direction. The transverse direction refers to directions orthogonal to the direction of beam propagation, also known as the xy-directions. In certain embodiments, the abutment face of patient interface 20 is selected as the xy-plane at z=0.

Scanner 16 may transversely direct the laser beam in any suitable manner. For example, scanner 16 may include a pair of galvanometrically-actuated scanner mirrors that can be tilted about mutually perpendicular axes. As another example, scanner 16 may include an electro-optical crystal that can electro-optically steer the laser beam. Scanner 16 may longitudinally direct the laser beam in any suitable manner. For example, scanner 16 may include a longitudinally adjustable lens, a lens of variable refractive power, or a deformable mirror that can control the z-position of the beam focus. The components of scanner 16 may be arranged in any suitable manner along the beam path, e.g., in the same or different modular units.

One (or more) optical elements 17 direct the laser beam towards focusing objective 18. An optical element 17 can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical element 17 is a mirror. Focusing objective 18 focuses the focal point of laser beam through the patient interface 20 towards a point of eye 22. In the example, focusing objective 18 is an objective lens, e.g., an f-theta objective.

Camera 38 records images of the movement of eye 22. Examples of camera 38 include a video, optical coherence tomography (OCT), or eye-tracking camera. Camera 38 delivers image data, which represent recorded images of the eye 22, to computer 30. Computer 30 may perform image processing on the image data to identify features of the eye to align the eye.

Light source 39 (39a, 39b) provides light to illuminate the surgical site. Light source 39 may have any suitable configuration that directs light towards the surgical site. In certain embodiments, light source 39 includes one or more lighting elements that provide illumination that is directed towards the field. The one or more lighting elements may partially or completely surround the field or may be placed above the field to illuminate the field. In the illustrated example, light source 39 includes embodiments 39a, 39b, and system 10 may have one, both, or neither of the embodiments. Light source 39a has an annular shape with a diameter that is substantially equivalent to the diameter of the top of patient interface 20. Light source 39b has an annular shape with a diameter that is substantially equivalent to the portion of patient interface 20 that source 39b encircles.

Patient interface 20 interfaces with the cornea of eye 22 to couple eye 22 to laser device 15. Patient interface 20 serves to fix eye 22 in place so the laser beam can treat eye 22. Patient interface 20 is described in more detail with reference to FIG. 2.

Computer 30 controls controllable components (e.g., laser source 12, scanner 16, optical elements 17, and/or focusing objective 18) in accordance with computer program 34. Computer program 34 includes computer code that instructs the controllable components to focus the laser beam at a region of the cornea and to photodisrupt at least a portion of the region.

Figure 2:
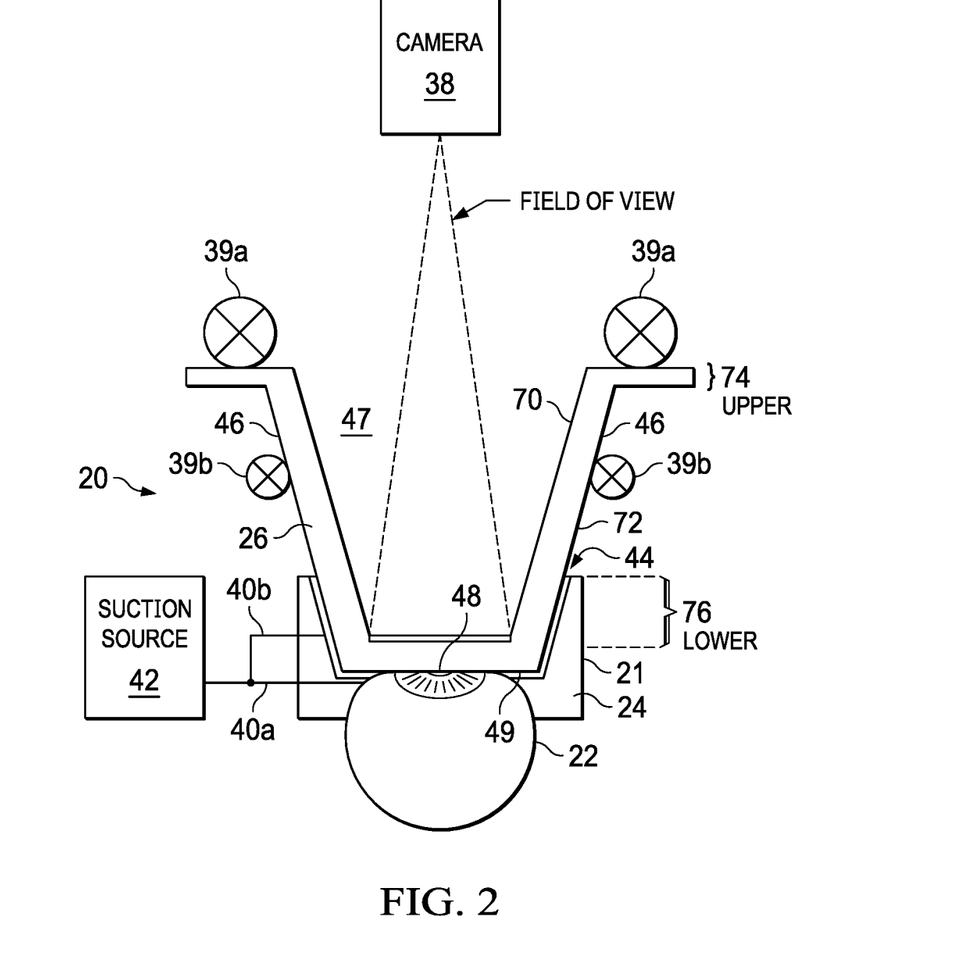
FIG. 2 illustrates an example of a patient interface according to certain embodiments.

FIG. 2 illustrates an example of patient interface 20. In certain embodiments, patient interface 20 includes an attachment portion 21 and an interface portion 26. Attachment portion 21 affixes patient interface 20 to eye 22 in any suitable manner, e.g., via suction or mechanical attachment. Interface portion 26 comes into contact with the cornea of eye 22, typically above the surgical site. Attachment portion 21 and interface portion 26 may be formed as one piece or may be formed as two or more separate pieces that accommodate each other.

In the example, patient interface 20 includes an attachment portion 21, which comprises suction ring 24, and an interface portion 26 coupled as shown. Suction ring 24 has a substantially annular shape with a ring axis and an opening 44. Suction ring 24 includes one or more evacuation channels 40 (40a, 40b) coupled to a suction source 42. Suction source 42 provides suction force. An evacuation channel 40 allows for suction to couple patient interface 20 to eye 22. In the example, the suction force through evacuation channel 40a affixes suction ring 24 to eye 22, and/or the suction force through evacuation channel 40b secures interface portion 26 to suction ring 24.

Interface portion 26 has a substantially frustoconical or cylindrical shape with a conical axis and a cone wall 46 that defines a cone interior 47. Interface portion 26 is shaped to at least partially fit within opening 44. Cone wall 46 has an inner surface 70 and an outer surface 72, where inner surface 70 defines cone interior 47. Cone wall 46 has an upper portion 74 and a lower portion 76, where lower portion 76 coupled to contact portion 48. Contact portion 48 has an abutment face 49 that comes into contact with the cornea of eye 22. Contact portion 48 may be translucent or transparent to the laser beam and has an abutment face 49 that interfaces with the cornea. Abutment face 49 is generally disposed outwardly from the surgical site. In certain embodiments, abutment face 49 is planar and forms a planar area on the cornea, which may define the xy-plane. In other embodiments, abutment face 49 need not be planar, e.g., may be convex or concave.

In certain embodiments, patient interface 20 has one or more structures that direct light from cone wall 46 towards cone interior 47 and/or central portion of contact portion 48 to illuminate a surgical site portion of interface 20 (e.g., a portion interface 20 in contact with the surgical site of the eye). The structures may have any suitable configuration. For example, a structure may be a diffusion structure disposed at inner surface 70 of the cone wall 46. The diffusion structure diffuses light traveling from cone wall 46 towards cone interior 47. As another example, a structure may be a reflective structure disposed at cone wall 46. The reflective structure reflects light towards cone interior 47. As another example, a structure may direct light within cone wall 46 towards lower portion 76. As another example, a structure may be disposed at contact portion 48 of interface portion 26. The structure directs light towards the center of contact portion 48. Examples of the structures are described in more detail with reference to FIGS. 3 to 6.

Figure 3A:
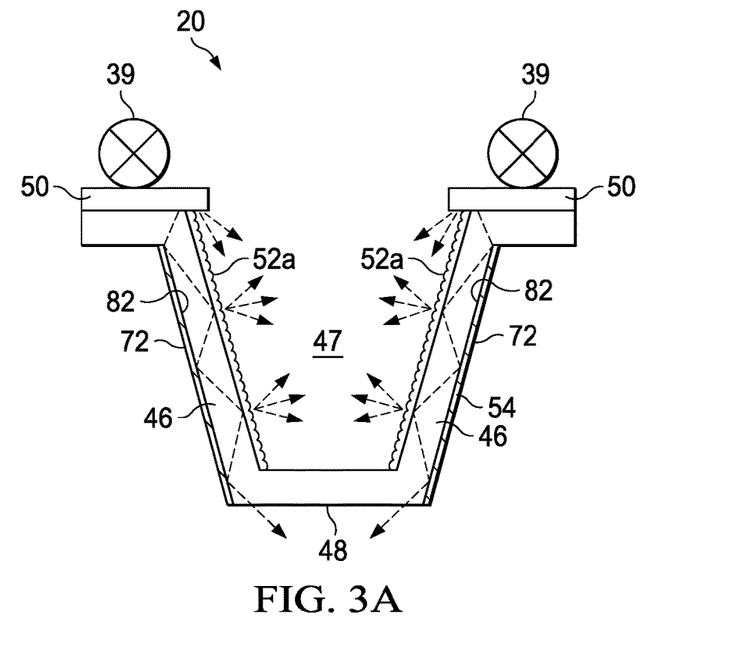
FIGS. 3A through 3C illustrate examples of diffusion and reflective structures of certain embodiments of the patient interface.
Figure 3B:
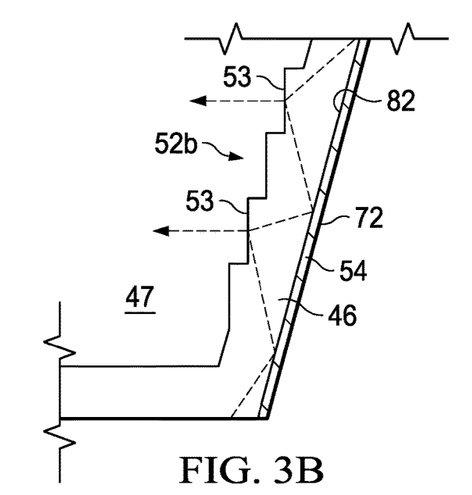
Figure 3C:
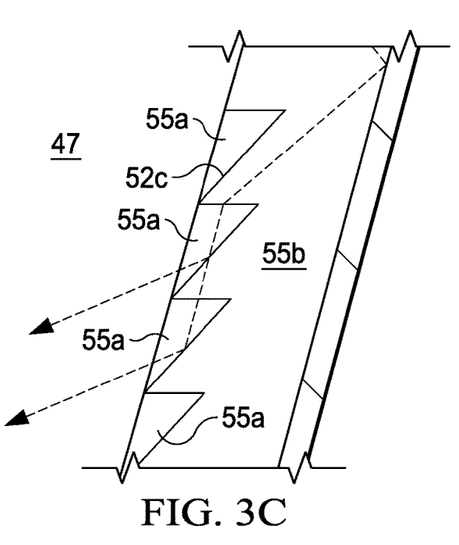

FIGS. 3A through 3C illustrate examples of diffusion structures 50 (50a-50c), 52 and a reflective structure 54 of certain embodiments of patient interface 20. A diffusion structure may be a structure of a material that diffuses light passing through the material by, e.g., refracting and/or scattering the light. In certain embodiments, a diffusion structure may be a structure of the surface of the material, such as a rough surface. The rough surface may be produced in any suitable manner. For example, the surface may be molded from a rough mold. As another example, a smooth surface may be roughened by rubbing it with a rough surface (e.g., sandpaper) or by etching it with a laser beam.

In other embodiments, a diffusion structure may be a structure within a material that diffuses light that passes through the material. For example, a diffusion structure may be photodisruptions made by a femtosecond laser beam. As another example, a diffusion structure may be changes in refraction in a material, which may be formed from material with different indices of refraction. In yet other embodiments, a diffusion structure may be a stepped feature, such as a grating, of inner surface 70 of the cone wall 46. A stepped feature may be a feature that has one, two, or more steps, where a step changes the direction of light. In yet other embodiments, a diffusion structure may be a stepped feature, such as a grating, formed within the cone wall 46 with material of different indices of refraction.

FIG. 3A describes a patient interface 20 that includes diffusion structures comprising a diffusion panel 50 and a diffusion structure 52a. Diffusion panel 50 comprises a transparent or semi-transparent material (e.g., plastic) that diffuses light from light source 39. Diffusion structure 52a is disposed at inner surface 70 of the cone wall 46 and diffuses light traveling from cone wall 46 towards cone interior 47.

In the example, patient interface 20 also includes reflective structure 54. Examples of a reflective structure 54 include a reflective surface 54, such as a mirror. In the illustrated example, reflective surface 54 comprises an outer reflective structure 82 disposed at outer surface 72 of cone wall 46. Outer reflective structure 82 reflects light towards inner surface 70. In the example, some of the light passes inner surface 70, some light is reflected back towards outer reflective structure 82, and/or some light passes through lower portion 76 of patient interface 20. The light that passes through lower portion 76 may illuminate docking of patient interface 20 to eye 22, the lowering of patient interface 20 towards eye 22 and affixing patient interface 20 to eye 22.

FIG. 3B describes a diffusion structure 52b that is a stepped feature (e.g., a grating) of inner surface 70 of the cone wall 46. Diffusion structure 52b has discrete exit regions for the light. In the example, the exit regions are the substantially vertical regions 53 of structure 52b. In the example, "vertical" refers to parallel to the z-axis when patient interface 20 is coupled to laser device 15.

FIG. 3C describes a diffusion structure 52c that is a stepped feature (e.g., a grating) formed within cone wall 46 from material 55 (55a, 55b) of different indices of refraction. In the example, material 55a has a different index of refraction than that of material 55b. As light travels through cone wall 46, the material refracts light towards cone interior 47.

Figure 4:
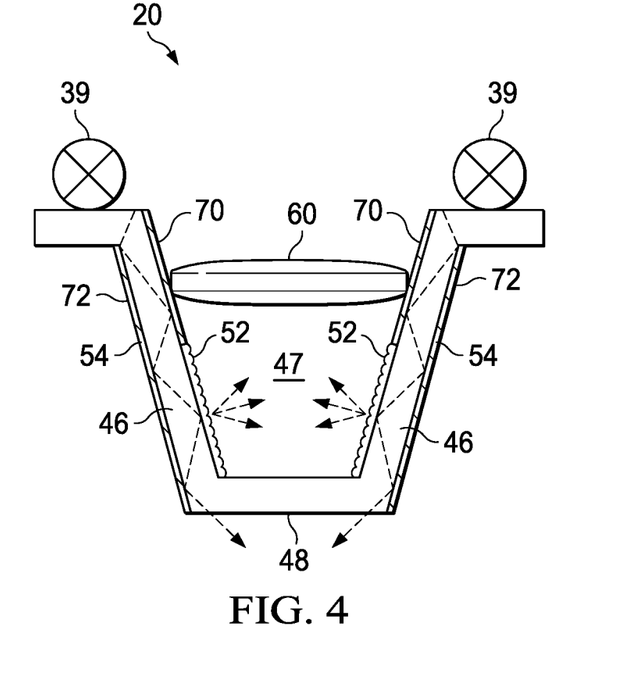
FIG. 4 illustrates an example of an arrangement of diffusion and reflective structures of certain embodiments of the patient interface.

FIG. 4 illustrates an example of an arrangement of diffusion structure 52 and reflective structure 54 of certain embodiments of patient interface 20. In the example, patient interface 20 includes an optical element 60, such as a lens. In certain embodiments, the lens may be a focusing lens for a treatment laser beam. Diffusion structure 52 and reflective structure 54 may be disposed at any suitable locations of patient interface 20 in any suitable arrangement. In the illustrated example, diffusion structure 52 is disposed at inner surface 70 between optical element 60 and contact portion 48. Diffusion structure 52 diffuses light traveling towards cone interior 47. Reflective structure 54 is disposed at outer surface 72 and inner surface 70 proximate to optical element 60 and towards the upper portion of patient interface 20. Reflective structure 54 disposed at outer surface 72 directs light towards inner surface 70, and reflective structure 54 disposed at inner surface 70 directs light towards reflective structure 54 disposed at outer surface 72.

Figure 5:
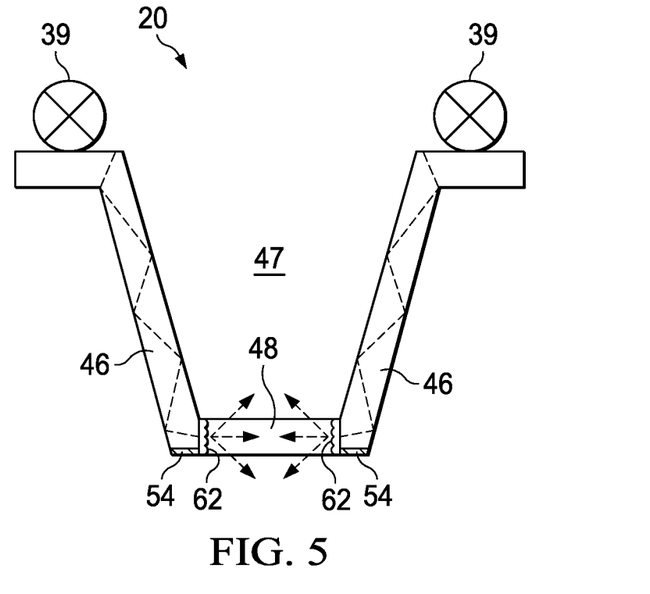
FIG. 5 illustrates examples of diffusion structures disposed at the contact portion of certain embodiments of the patient interface.

FIG. 5 illustrates an example of diffusion structures 62 disposed at contact portion 48 of certain embodiments of patient interface 20. A diffusion structure 62 diffuses light traveling towards the center of contact portion 48. In certain embodiments, contact portion 48 also includes a reflective structure 54 disposed at the portion of abutment face 49 adjacent to cone wall 47. Reflective structure 54 reflects light towards diffusion structure 62.

Figure 6:
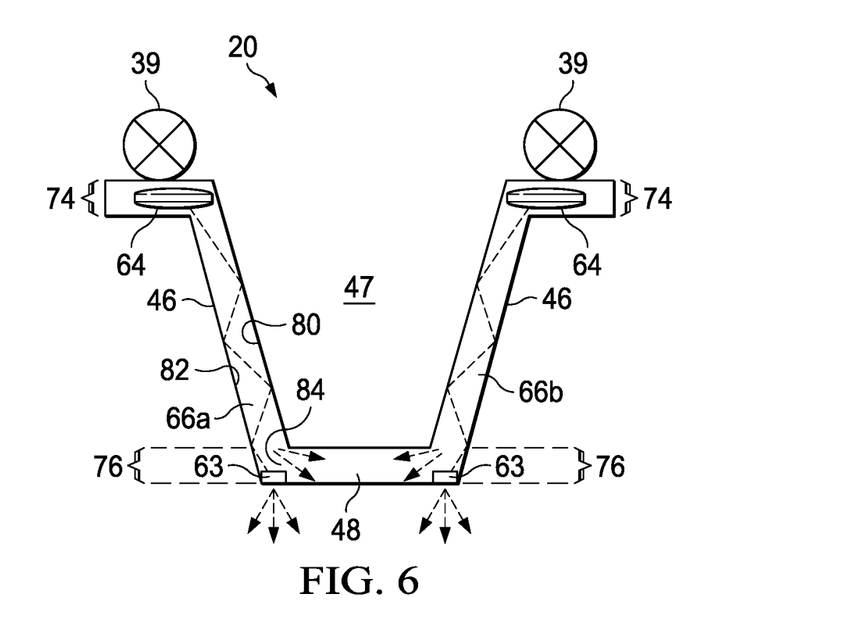
FIG. 6 illustrates an example of a light guide of certain embodiments of the patient interface.

FIG. 6 illustrates an example of a light guide 66 (66a) of certain embodiments of patient interface 20. Light guide 66a directs light within cone wall 46 from upper portion 74 towards lower portion 76 of patient interface 20. In the example, patient interface 20 includes an optical element 64 (e.g., a lens) directs light towards cone wall 46. Light guide 66a may comprise reflective structures 54 that include an inner reflective structure 80 and an outer reflective structure 82 arranged to direct light from upper portion 74 to lower portion 76. Inner reflective structure 80 is disposed at inner surface 70 of cone wall 46 and reflects light towards outer reflective structure 82. Outer reflective structure 82 is disposed at outer surface 72 of cone wall 46. Some light passes through a portion 84 of inner surface 70 that is free from inner reflective structure 80 towards the center of contact portion 48.

In the example, patient interface 20 also includes diffusion structures such as scattering structures 63. Scattering structures 63 scatters light in the z-direction, i.e., towards eye 22. This illumination may facilitate docking of patient interface 20 to eye 22, i.e., the lowering of patient interface 20 towards eye 22 and affixing patient interface 20 to eye 22.

Figure 7A:
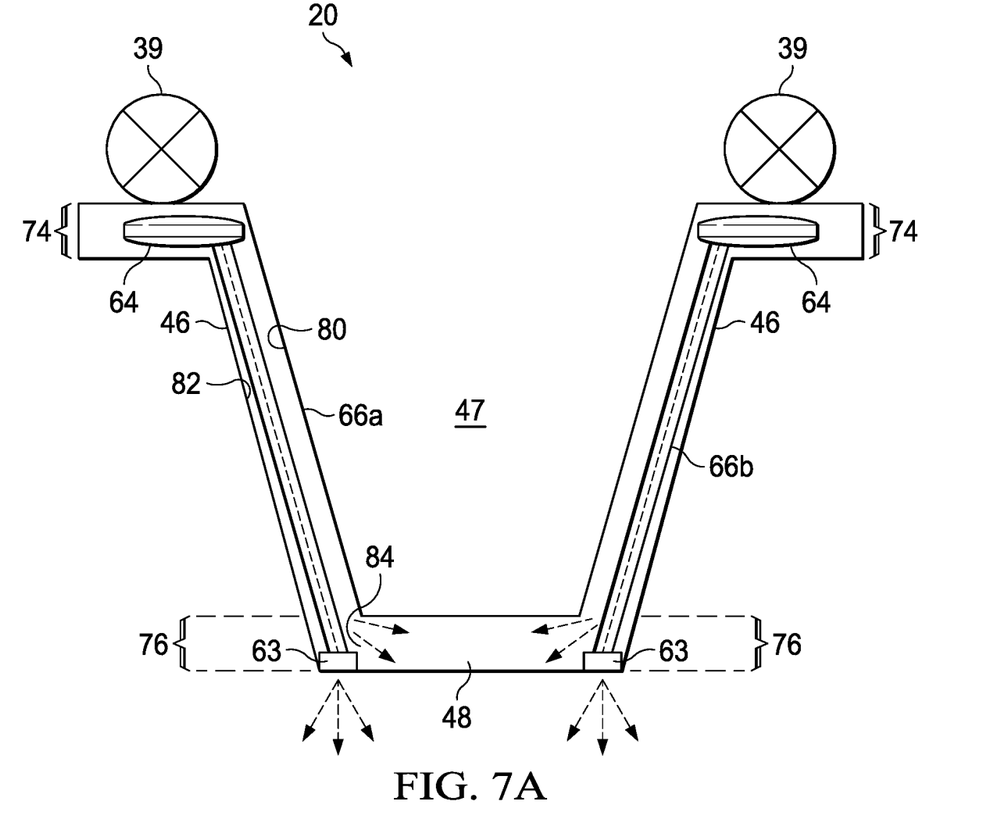
FIGS. 7A through 7C illustrate other examples of a light guide of certain embodiments of the patient interface.
Figure 7B:
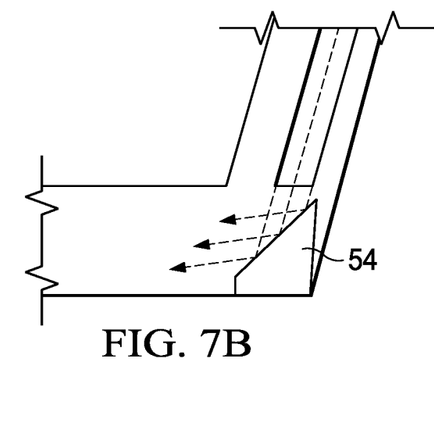
Figure 7C:
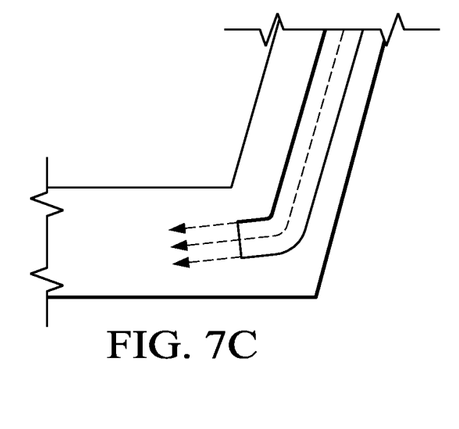

FIGS. 7A through 7C illustrate examples of a light guide 66 (66b) of certain embodiments of patient interface 20. FIG. 7A describes an example of light guide 66b that directs light within cone wall 46 from upper portion 74 to lower portion 76 of patient interface 20. In the example, patient interface 20 includes an optical element 64 (e.g., a lens) directs light towards light guide 66b. Light guide 66b directs light from upper portion 74 to lower portion 76. In certain examples, as light guide 66b reaches lower portion 76, light guide 66b may direct light towards cone interior 47 and/or towards the center of contact portion 48. Examples of light guide 66b include an optical fiber, e.g., a step-index or gradient-index fiber. In the example of FIG. 7A, patient interface 20 also includes scattering structures 63, similar to those of FIG. 6.

FIG. 7B describes a reflective structure 54 in place of scattering structures 63 of FIG. 7A. Reflective structure 54 reflects light towards cone interior 47 and/or towards the center of contact portion 48.

FIG. 7C describes a light guide 66b that is shaped (e.g., curved) to direct light towards cone interior 47 and/or towards the center of contact portion 48.

Figure 8A:
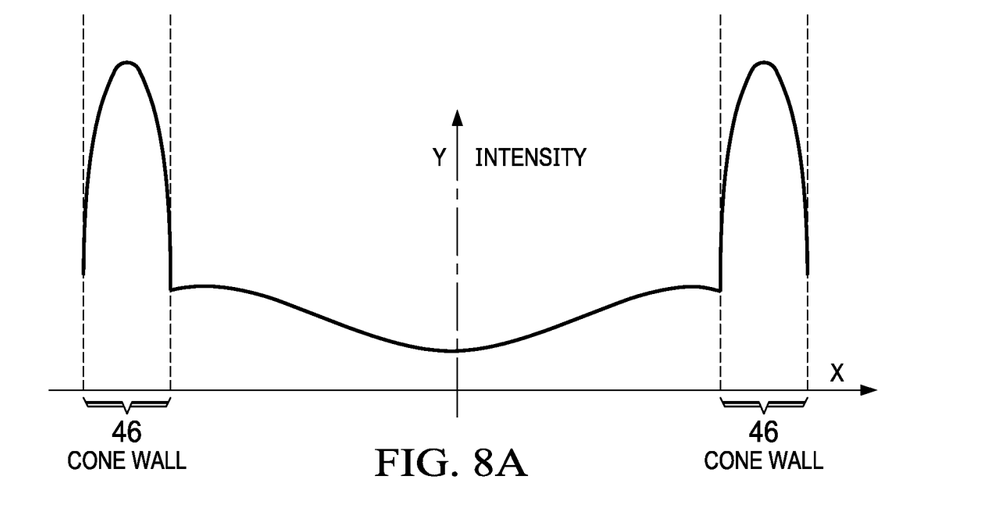
FIGS. 8A and 8B are graphs comparing the brightness distributions for patient interfaces without and with structures that distribute light.
Figure 8B:
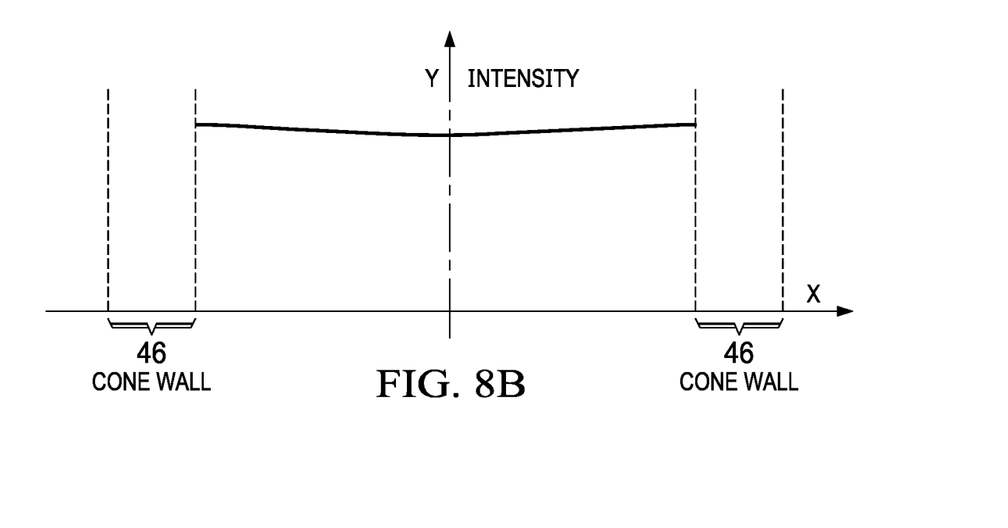

FIGS. 8A and 8B are graphs comparing the brightness distributions for a patient interface without a structure that distributes light and for a patient interface with a structure that distributes light. The y-axis represents the intensity of the illumination at contact portion 48 of patient interface 20, and the x-axis represents the position along a diameter of contact portion 48.

FIG. 8A describes the brightness distribution for a patient interface that does not include structures that direct light from cone wall 46 toward cone interior 47. Most light remains at cone wall 46, yielding decreased, inhomogeneous illumination at the surgical site.

FIG. 8B describes the brightness distribution for a patient interface 20 that does include structures that direct light from cone wall 46 toward cone interior 47. Light is directed away from the cone wall to illuminate the surgical site in a more homogenous manner. In certain embodiments, the structures for a particular interface design may be placed to yield a substantially homogeneous (i.e., uniform) brightness distribution across contact portion 48. In other embodiments, structures for a particular interface design may be placed to yield more brightness in a particular area of contact portion 48. For example, more brightness may be desired at a surgical site portion of contact portion 48, e.g., a portion that is in contact with the surgical site of the eye. This portion may be substantially centered in contact portion 48 with a radius that is less than 25%, 25% to 50%, 50% to 75%, and/or 75% to 95% of the radius of contact portion 48.

Increased and/or more homogeneous brightness in the area of the eye in contact with abutment face 49 may yield more accurate and/or precise imaging by camera 38. The increased and/or more homogeneous brightness may also yield more efficient and/or reliable identification of features (e.g., e.g., vessels, iris structures, pupil edge, or limbus edge) that may be used to align the eye.

A component (such as computer 30) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface (e.g., a Graphical User Interface (GUI)) is a type of interface that a user can utilize to interact with a computer. Examples of user interfaces include a display, touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. A patient interface for an ophthalmic laser system, comprising:
    an interface portion comprising:
        a contact portion with an abutment face, the abutment face configured to be in contact with a cornea of an eye, the contact portion having a surface on a side opposite of the abutment face;
        a cone wall disposed outwardly from the contact portion, the cone wall defining a cone interior, the cone wall having an inner surface and an outer surface, the inner surface and the surface on the side opposite of the abutment face defining the cone interior, the cone wall having an upper portion and a lower portion, the lower portion coupled to the contact portion, the cone wall comprising one or more structures configured to direct illumination light from within the cone wall towards the cone interior, the one or more structures comprising a stepped feature between the inner surface and the outer surface of the cone wall, the stepped feature formed by at least two materials of the cone wall, the materials having different indices of refraction, the stepped feature comprising a plurality of steps, each step changing a direction of the illumination light; and
    an attachment portion configured to affix the interface portion to the cornea of the eye.

2. The patient interface of claim 1, the one or more structures further comprising an inner surface stepped feature of the inner surface of the cone wall.

3. The patient interface of claim 1, each of the steps comprising a horizontal region.

4. The patient interface of claim 1, each of the steps comprising a horizontal region and a non-horizontal region.

5. The patient interface of claim 1, the one or more structures further comprising a diffusion structure disposed at the inner surface of the cone wall, the diffusion structure being a structure of a material of the cone wall that diffuses illumination light passing through the material, the diffusion structure configured to diffuse illumination light traveling from the cone wall towards the cone interior.

6. The patient interface of claim 1, the one or more structures further comprising a reflective structure disposed at the cone wall, the reflective structure comprising a reflective surface configured to reflect illumination light towards the cone interior.

7. The patient interface of claim 6, the reflective structure disposed at the inner surface of the cone wall.

8. The patient interface of claim 6, the reflective structure disposed at the outer surface of the cone wall.

9. The patient interface of claim 1, the one or more structures configured to direct illumination light within the cone wall towards the lower portion.

10. The patient interface of claim 1, the one or more structures further comprising a light guide configured to direct illumination light within the cone wall towards the lower portion.

11. The patient interface of claim 1, the one or more structures further comprising a plurality of reflective structures configured to direct illumination light within the cone wall towards the lower portion, each reflective structure comprising a reflective surface, the plurality of reflective structures comprising an inner reflective structure and an outer reflective structure:
    the inner reflective structure disposed at the inner surface of the cone wall, the inner reflective structure configured to reflect illumination light towards the outer reflective structure; and
    the outer reflective structure disposed at the outer surface of the cone wall, the outer reflective structure configured to reflect illumination light:
        towards the inner reflective structure; and
        through a portion of the inner surface that is free from the inner reflective structure.

12. The patient interface of claim 11, the one or more structures further comprising a diffusion structure disposed at the portion of the inner surface that is free from the inner reflective structure, the diffusion structure configured to diffuse illumination light travelling from the cone wall towards the cone interior.

13. The patient interface of claim 1, the contact portion of the interface portion comprising a contact portion structure configured to direct illumination light towards a surgical site portion of the contact portion.

14. The patient interface of claim 13, the contact portion structure comprising a reflective structure disposed at the portion of the abutment face adjacent to the cone wall.

15. The patient interface of claim 1, the one or more structures comprising a diffusion structure configured to refract illumination light towards a surgical site portion of the contact portion, the diffusion structure being a structure of a material of the cone wall that refracts light passing through the material.

16. The patient interface of claim 1, the one or more structures comprising a diffusion structure configured to scatter illumination light towards a surgical site portion of the contact portion, the diffusion structure being a structure of a material of the cone wall that scatters light passing through the material.

17. A patient interface for an ophthalmic laser system, comprising:
    an interface portion comprising:
        a contact portion with an abutment face, the abutment face configured to be in contact with a cornea of an eye, the contact portion having a surface on a side opposite of the abutment face;
        a cone wall disposed outwardly from the contact portion, the cone wall defining a cone interior, the cone wall having an inner surface and an outer surface, the inner surface and the surface on the side opposite of the abutment face defining the cone interior, the cone wall having an upper portion and a lower portion, the lower portion coupled to the contact portion, the cone wall comprising one or more structures configured to direct illumination light from within the cone wall towards the cone interior, the one or more structures comprising a stepped feature of the inner surface of the cone wall, the stepped feature comprising a plurality of steps, each step changing a direction of the illumination light; and an attachment portion configured to affix the interface portion to the cornea of the eye.

18. The patient interface of claim 17, the one or more structures further comprising a diffusion structure configured to scatter illumination light towards a surgical site portion of the contact portion, the diffusion structure being a structure of a material of the cone wall that scatters light passing through the material.

19. The patient interface of claim 17, the one or more structures further comprising a diffusion structure configured to scatter illumination light towards the eye, the diffusion structure being a structure of a material of the cone wall that scatters light passing through the material.

20. The patient interface of claim 17, the one or more structures further comprising a reflective structure comprising a reflective surface configured to reflect illumination light towards a surgical site portion of the contact portion.

21. The patient interface of claim 17, the one or more structures further comprising a light guide configured to direct light within the cone wall from the upper portion towards the lower portion.

22. The patient interface claim 21 the light guide curved to direct illumination light towards a surgical site portion of the contact portion.

23. The patient interface of claim 17, each step of the plurality of steps comprising a vertical exit region.

* * * * *